US006820058B2

(12) United States Patent
Wood et al.

(10) Patent No.: US 6,820,058 B2
(45) Date of Patent: Nov. 16, 2004

(54) METHOD FOR ACCELERATED PROVISION OF FUNDS FOR MEDICAL INSURANCE USING A SMART CARD

(76) Inventors: Richard Glee Wood, 4627 Cashel Cir., Houston, TX (US) 77069; Wesley Jack White, Jr., 6219 Squires Ct., Spring, TX (US) 77389

( * ) Notice: Subject to any disclaimer, the term of this patent is extended or adjusted under 35 U.S.C. 154(b) by 142 days.

(21) Appl. No.: 10/303,631

(22) Filed: Nov. 25, 2002

(65) Prior Publication Data

US 2004/0103062 A1 May 27, 2004

(51) Int. Cl.[7] .............................................. G06F 17/60
(52) U.S. Cl. ................................................ 705/4; 705/2
(58) Field of Search ........................ 705/2, 3, 4; 283/54

(56) References Cited

U.S. PATENT DOCUMENTS

| | | | | |
|---|---|---|---|---|
| 5,884,271 A | * | 3/1999 | Pitroda ........................... | 705/1 |
| 6,012,035 A | * | 1/2000 | Freeman et al. ................ | 705/2 |
| 6,163,770 A | | 12/2000 | Gamble .......................... | 705/4 |
| 6,208,973 B1 | * | 3/2001 | Boyer et al. .................... | 705/2 |

FOREIGN PATENT DOCUMENTS

| WO | WO 02/075627 A1 | * | 9/2002 | ........... G06F/17/60 |
|---|---|---|---|---|

OTHER PUBLICATIONS

Boyd, Health insurance for animals is available, Sep. 1997, Star Tribune, p. 08E.*
Rehnquist, Janet. "Improper Fiscal year 2002 Medicare Fee–for–Service Payments," Jan. 8, 2003, (A17–02–02202).
Eiland, "A Bill to be Entitled an Act." Acts of the 75th Legislature, Regular Session, 1997.
"Texas Senate Special Committee on Prompt Payment of Health Care Providers." Interim Report to the 78th Legislature, Nov. 2002.

* cited by examiner

Primary Examiner—Joseph Thomas
Assistant Examiner—Christopher L. Gilligan
(74) Attorney, Agent, or Firm—Wendy Buskop; Buskop Law Group, P.C.

(57) ABSTRACT

The invention is a method for accelerating the provision of funds to a service provider for medical insurance using a smart card by a person obtaining medical insurance coverage from an insurer and obtaining a contract from the service provider, creating a smart card, using the smart card to see if the user is eligible for funds, to see if the medical service is preauthorized, and to see if service provider is preauthorized, transmitting acknowledgment of services from service provider to insurer, transmitting amount from insurer to service provider, transmitting acknowledgement of amount from service provider to insurer, and transferring payment quickly from insurer to service provider.

16 Claims, 6 Drawing Sheets

METHOD FOR ACCELERATED PROVISION OF FUNDS FOR MEDICAL INSURANCE USING A SMART CARD

FIELD OF THE INVENTION

The present invention relates to a method for providing funds, as an advance against proposed charges, using a card known as a smart card that contains identification and other information in order to eliminate fraud on insurance companies.

BACKGROUND OF THE INVENTION

Physicians have traditionally had to wait long periods of time to get paid for their medical services. Physicians, physical therapists and others have been required to extend credit to individuals with insurance in order to get paid. This situation has become tedious and caused health care costs to be very high.

Pharmacists have had the use of automated services, such as the TelePAID system. The TelePAID system offered by PAID prescriptions LLC is a system that uses a plastic card that contains only a group number. A pharmacist, in turn, manually enters the group number, member number, and prescription information, in as attempt to give the card holder the lowest customer price into the system. The pharmacist then provides the customer with the prescription and collects the approved amount from the TelePAID system. The customer is given a receipt including authorization number. This system has the insured paying for the balance. A need has long existed for a system, wherein the insurer advances funds so that the insured does not have to handle money.

This need has been particularly great for incapacitated individuals, such as those in nursing homes, who are no longer able to handle funds or complicated transactions.

The cost of health care continues to increase as the health care industry becomes more complex, specialized, and sophisticated. The proportion of the gross domestic product that is accounted for by health care is expected to gradually increase over the coming years as the population ages and new medical procedures become available.

Over the years, the delivery of health care services is not only from individual physicians but also from large managed health maintenance organizations, hospitals, pharmacists, mental health therapists, and pharmacists. There are growing numbers of medical, dental, and pharmaceutical specialists in a complex variety of health care options and programs to service the increasing populations, which has increased in elderly populations.

Unfortunately, the payment for the delivered health care is now occurring much later than the delivery of the service. Increasingly, health care providers are acting as credit institutions for the insured because of the lack of insurers to timely provide funds under a policy.

The cost of supporting patient costs has increased during recent years, thereby contributing to today's costly health care system. A significant portion of the increase in the cost of medical service is caused by the administrative costs represented by the systems for creating, reviewing and adjudicating health care provider payment requests. Such payment requests typically include bills for procedures performed and supplies given to patients. Currently, the systems for reviewing and adjudicating payment requests represent additional health care transaction costs that directly reduce the efficiency of the health care system and increases the cost of the health care delivered.

A need exists to reducing the magnitude of transaction costs involved in reviewing and adjudicating payment requests that would have the effect of reducing the rate of increase of health care costs.

A need exists for streamlining payment request review and adjudication that would also positively increase the portion of the health care dollar that is spent on treatment rather than administration.

A need exists to reduce the traditionally high cost of health care administration, including the review and adjudication of payment requests which results from health care service providers having to act as "banks" or "credit sources" for patients.

A need exists to facilitate the understanding of the contractual obligations between the service provider and the insured. Often, there are many different contractual arrangements between different patients, insurers, and health care providers. The amount of authorized payment may vary by the service or procedure, by the particular contractual arrangement with each health care provider, by the contractual arrangements between the insurer and the patient regarding the allocation of payment for treatment, and by what is considered consistent with current medical practice.

During recent years, the process of creating, reviewing, and adjudicating payment requests from health care providers has become increasingly automated. For example, there exist claims processing systems whereby technicians at health care providers' offices electronically create and submit medical insurance claims to a central processing system. The technicians include information identifying the physician, patient, medical service, insurer, and other data with the medical insurance claim. The central processing system verifies that the physician, patient, and insurer are participants in the claims processing systems. If so, the central processing system converts the medical insurance claim into the appropriate format of the specified insurer, and the claim is then forwarded to the insurer. Upon adjudication and approval of the insurance claims, the insurer initiates a check to the provider. In effect, such systems bypass the use of the mail for delivery of insurance claims. However, there is no known system for accelerated payment of funds within only a day or two of the claims presentation.

In partially automated systems, such as that described in the foregoing example, the technician can submit a claim via electronic mail on the Internet or by other electronic means. To do so, the technician establishes communication with an Internet service provider or another wide area network. While communication is maintained, the technician sends the insurance claim to a recipient and then either discontinues communication or performs other activities while communication is established. Using such conventional systems, personnel at the health care provider's office are unable to determine whether the submitted claim is in condition for payment and do not receive any indication, while communication is maintained, whether the claim will be paid.

Because of the large number of insurers and insurance plans, the amount of the co-payment can vary from patient to patient and from visit to visit. Moreover, when a patient is not covered for a certain treatment, the patient may be liable for the entire amount of the health care services. It is sometimes difficult for technicians at the offices of the health care provider to determine that amount of any co-payment or any other amount due from the patient, such as a deductible that must be collected while the patient remains at the offices after a medical visit. Once the patient leaves the office, the expense of collecting amounts owed by patients increases and the likelihood of being paid decreases. Conventional insurance claim submission systems have not been capable of efficiently and immediately informing technicians at the offices of a health care provider of amounts owed by patients, particularly when the amount is not a fixed dollar amount. A need has been desired, particularly by patients (insured) and health care providers for a solution to this dilemma.

Other methods and apparatus exist to attempt to streamline the insurance claim payment process, such as the method disclosed in Gamble U.S. Pat. No. 6,163,770. This patent reveals using a digital electrical apparatus to generate output for insurance documentation for a first insurance policy having a first risk and claims while revealing a concurrent second insurance policy for a second risk, wherein the second risk is different from the first. The processor of this method is connected to a memory device for storing and retrieving operations including machine-readable signals in the memory device, to an input device for receiving input data and converting the input data into input electrical data, to a visual display unit for converting output electrical data into output having a visual presentation, to a printer for converting the output electrical data into printed documentation, wherein the processor is programmed to control the apparatus to receive the input data and to produce the output data by steps including: inputting actuarial assumptions defining the first insurance policy; and computing a value of a specific financial attribute of the first insurance policy; the method further including the step of inserting the value of the financial attribute in the first insurance policy and other printed documentation related to the first insurance policy.

In view of the foregoing, there is a need for more a fully automated claims processing system that have the ability to have an accelerated pay schedule and an ability to reduce the uncertainty as to whether a claim to be submitted is likely to be paid or rejected.

Further, security is an issue of paramount importance in electronic communication. The card containing many elements personal and private information must be secure from all types of intrusion by unwarranted attempts to access. Only the owner of the card can give permission to read the card and establish the communication links to the owner's private files at the insurer or any other location where information may reside. This activity must be incompliance with all applicable privacy laws and the card and its security must have the ability to change along with laws should a change occur. There are other medical laws that also must be complied with in example HIPAA (sp) and others of the like are federal compliance requirements. The card will help facilitate that compliance. Again the need for security is paramount.

The present invention has been developed to provide an accelerated claims processing system that would more easily allow health care providers to know what patient and treatment information must accompany insurance claims, whether or not a patient is eligible for accelerated fee payment, and to obtain funds quickly against rendered services from insurance companies. The present invention also includes various elements to provide security for the user.

SUMMARY OF THE INVENTION

The invention relates to a method for accelerating the provision of funds to a service provider from medical insurance using a smart card, comprising the steps of: obtaining medical insurance coverage from an insurer for a person; creating a smart card for the person, wherein the smart card comprises: information about medical insurance coverage for the person and a personal identification code.

Next, the smart card is used to determine if the person is eligible for accelerated provision of funds from the insurer to a service provider for medical services based on medical insurance coverage.

The smart card is used to determine if a medical service is preauthorized by the insurer for the person.

The smart card is used to determine if a service provider is preauthorized by the insurer to perform a medical service. Once these determinations are made, the smart card facilitates a first transmission from the service provider to the insurer. The first transmission can include information relative to medical service costs, information on the medical services provided to the insured; and an acknowledgement that the medical service has been rendered from the service provider to the person.

The smart card facilitates the receipt of a second transmission from the insurer to the service provider. The second transmission preferably comprises the amount of payment required by the person based on the insurance coverage. In addition, the smart card facilitates a third transmission to the insurer from the service provider. This third transmission comprises an acknowledgement that the amount of payment required by the person is based on the insurance coverage, such as the co-payment or the deductible amount. On approximately the same day that the third transmission is received by the insurer, funds are transmitted from the insurer to the service provider for the medical service provided to the person.

BRIEF DESCRIPTION OF THE DRAWINGS

The present invention will be explained in greater detail with reference to the appended figures, in which.

Figure 1:
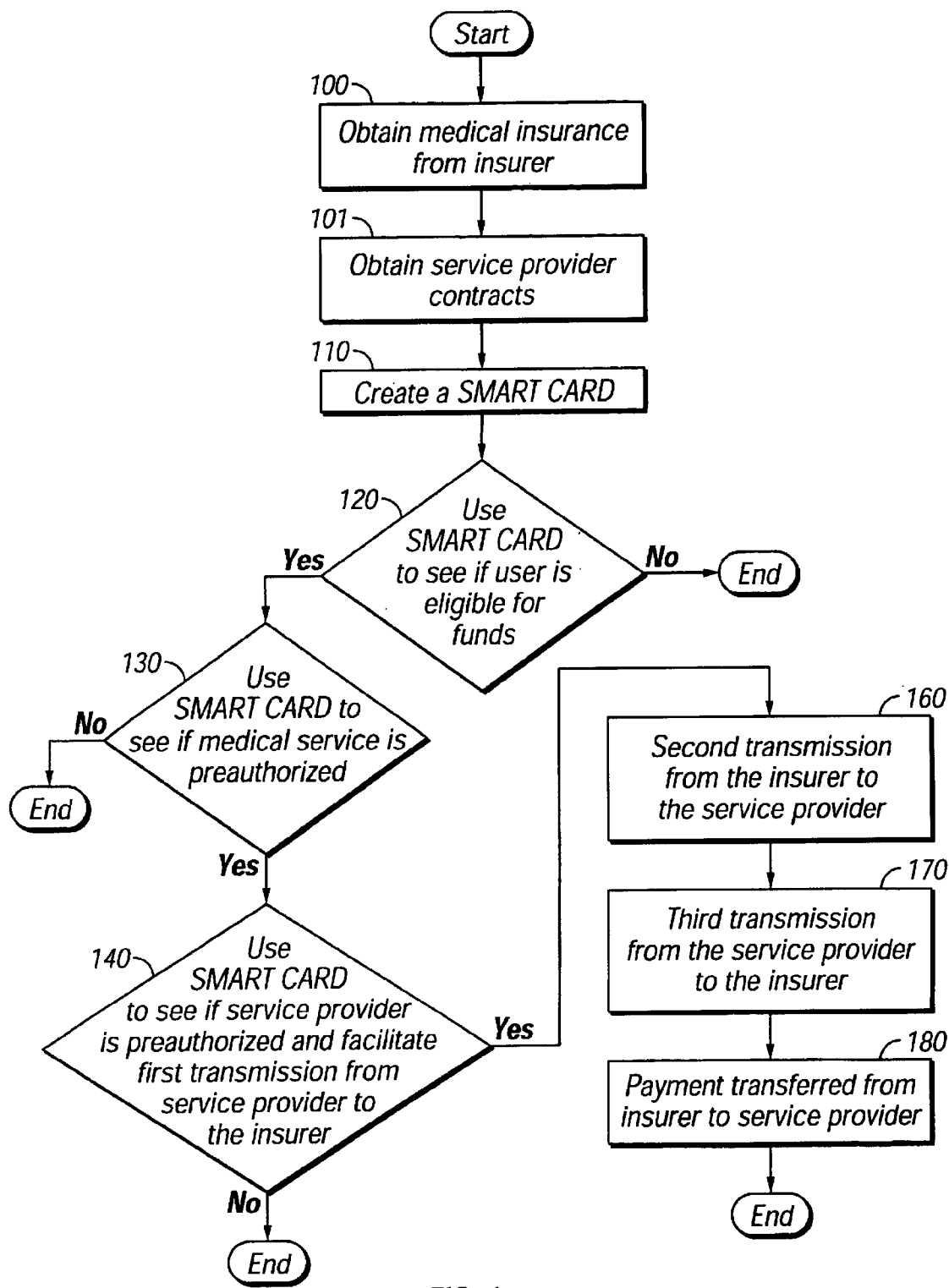
FIG. 1 is a diagram of the overall method of the invention.

The present invention is detailed below with reference to the listed Figures.

DETAILED DESCRIPTION OF THE PREFERRED EMBODIMENTS

Before explaining the present invention in detail, it is to be understood that the invention is not limited to the particular embodiments and that it can be practiced or carried out in various ways.

The invention relates to a method for accelerating the provision of funds to a service provider from medical insurance using a smart card. This means, the method relates to the provision of money, such as $75 for an office visit, to a general practice physician from medical insurance, such as a United Health Care Select Plus POS™ using a plastic card with a chip in it containing information on the insured. It is also contemplated that a plastic smart card could be used with a magnetic strip without a chip.

The invention advantageously reduces fraud on insurance companies by eliminating physician or service provider's inadvertent creation of non-patients, people who do not exist, and eliminates non-service lodes for billing service that were not rendered. Advantageous the invention permits a comparison of the list of doctors, patients, and the insurer's records for easy audit. Also dates of service approved could be compared to services performed dates to audit record and reduce fraud.

The steps of this method include first obtaining medical insurance coverage from an insurer for a person.

Typical medical insurance coverage can be government medical insurance coverage, such as a United States medical insurance, known as Medicare or Medicaid, or it can be state government insurance, such as a Texas Employer's Insurance, or even private medical insurance coverage, such as Guardian medical insurance or United Health Care Insurance. Typically, a person completes an application for insurance through their employer or individually and submits the information as premium to the insurance company. A policy is then issued to the person for the insurance coverage. The policy can be an individual policy or a group policy.

Next, a smart card is created for the insured. For the chip version of the smart card, the card is first manufactured in a conventional manner, and then the relevant information is downloaded from the computers of the insurance company to the card. For a non-chip version of a smart card, the card manufacturer would be provided information about the insured from the insurance company and embed the relevant information in the magnetic strip and then mail or transfer the magnetic strip card to the user.

The insured can be the primary insured, a spouse, a non-married "significant partner", at least one dependent, such as a one or more children, or it can be combinations of these.

It is also contemplated to be within the scope of the invention that the primary insured can be an animal, such as a thoroughbred horse, like Secretariat the winning race horse, a famous breeding bull or some other type of registered pure-bred animal, such as an American Kennel Club (AKC) registered animal. The primary insured, if an animal can be linked with an appropriate animal insurance policy, such as those available through the AKC.

The smart card can contain information about medical insurance coverage for the insured (person or animal) and a personal identification code, such as a personal identification number or "PIN".

The smart card is an electronically readable card and can connect to the service provider of the insurance contract, and may be via the Internet or telephone line. The card is contemplated to preferably contain information on at least one or more of the following:

a. insured name (example—Richard Wood);
b. insured address (example—2396 Wood Street, Houston, Tex. 77019);
c. insured phone (example—713-323-5555);
d. insured fax (example—713-323-5554);
e. insured email (example—Wood@aol.com);
f. insurer name or plan manager name (example—a privately funded plan such as Klein Independent School District Employee Benefit Plan of Texas);
g. insurer address or plan manager's address (example—the address for the Klein plan PO Box 672528, Houston, Tex. 77267);
h. insurer phone or plan manager's phone (example—281-873-8682);
i. optionally, the insurer fax or plan manager's fax;
j. optionally, insurer e-mail or plan manager's email;
k. insurer's website or plan manager's website (example—www.hasonline.com);
l. insurer claims representative or plan manager's representative (example—Health Administration Services, Inc.);
m. type of plan (example—PPO);
n. insured policy number or plan number (example—Group 200116289.);
o. insured group number or group plan number (example—KLINASD);
p. insured's co-pay amount (example—$25);
q. insured deductible amount (example—$500 deductible);
r. insured's medical history (example—allergy to penicillin);
s. instructions (example—pre-certification instructions or urgent admission instructions or emergency admission instructions can be embedded in the card);
t. other phone numbers (example—a phone number for prescription information, a phone number to locate qualified pharmacies under the plan, a phone number to call an approved pharmacist, a phone number to talk to a insurer's nurse, a phone number for mental health questions, and/or a phone number for chemical dependency);
u. issue date or "validity" date;
v. an expiration date or "expiry date";
w. statements as to ownership of the card;
x. statements as to eligibility of the holder as to the rights of the card and the existence of written agreements related to the card; and
y. disclaimers concerning use, misuse and revocation of the card.

Alternatively, electronic claims submission information through WebMD or THIN that would have a payer identification number can be embedded in the card. It should be noted that some plans have many choices of plans, for example, the Klein plan has choices including Heath Administration Services Med-watch Program for hospital confinements, HHPO (a Health Administration Services Select Hospital Network), an Immediate Care Prescription Program, and a Mail Order Pharmacy Program. All this information can be embedded on the smart card. Alternatively other codes can be embedded in the card, such as a other prescription codes, including the basic insurance number (BIN) number.

Additionally, the card can include complete or partial information on the insured's medical history, such as, but not limited to, information on health allergies, like allergies to penicillin and health problems, such as an insured has diabetes or has high blood pressure or even very low blood pressure. The card can include "health alerts" such as those concerning the taking a blood thinner, or any other prescription medications that a doctor or emergency room person should particularly be aware of. Additionally, information concerning whether or not the insured has allergies to two or more prescription drugs can be contained in the card.

The smart card can also contain information on funds which are available from an insurer for a completed authorized medical service for a particular patient. For example, the card can contain information on the "accelerated fund payment schedule" or the typical payment schedule for a particular medical service if the two differ. Generally, the phrase "completed authorized medical service" is considered to be a service which has been authorized by contract by the insurer or is a stated item of coverage in an insurance policy, such as "all dental cleanings are priced at $35".

The accelerated fund payment schedule could be a 100% payment schedule or a partial accelerated fund payment schedule depending on the contract with the insurer. It is contemplated that the funds would move electronically from the insurer's bank account to the service provider's bank account, such as by wire transfer, or similar normal electronic banking procedures.

Additionally, the smart card can contain information about the various insurance coverages held by the insured. An insured person can have insurance that could cover dental coverage, medical coverage, mental health, prescription drugs, nursing care, emergency room procedures and the like.

In the method, the smart card is used to determine if the person is eligible for accelerated provision of funds from the insurer to a service provider for medical services based on medical insurance coverage.

Additionally, the smart card can be used to determine if a medical service is preauthorized by the insurer for the person, such as for a "John Doe", who is preauthorized for all chest x-rays without need for additional authorization from the insurer.

The smart card can be used to determine if a service provider is preauthorized by the insurer to perform a medical service. For example, the smart card can contain information the all blood work related to sugar testing is pre-approved by the insurer.

The smart card is used to not only contain the information described above, but to link to the insurer's database and between the insurer's database and the service provider's database and the service provider's bank account. The smart card facilitates a first transmission from the service provider to the insurer. This first transmission can include information on:

i. determination that the card is valid and the person is eligible;
  ii. determination that the service provider is authorized to provide the service;
  iii. proposed medical service costs;
  iv. information on the medical services; and
  v. an acknowledgement that at least one medical service has been rendered from the service provider to the person.

The smart card facilitates the receipt of a second transmission from the insurer to the service provider. This second transmission can contain information on the amount of payment required by the person based on the insurance coverage. The amount of payment can be all or part of a co-payment fee, all or part of a deductible fee and combinations of these fees.

The smart card facilitates a third transmission to the insurer from the service provider. This third transmission would include an acknowledgement that the amount of the co-payment and the deductible have been paid by the person to the service provider thereby initiating payment by the insurer.

It should be noted that in the context of this invention, the insurer is considered an entity that has been authorized by the federal government or a state board of insurance to deliver insurance benefits for medical care.

Additionally, the insurer, as a set in the process, must make contracts with various service providers, such as pharmacists, nurses, doctors, nursing homes that can be linked to the smart card.

The method involves that on approximately the same day that the third transmission is received by the insurer, or perhaps on or a few days later, funds are then transmitted from the insurer to the service provider for the medical service provided to the person. This accelerated payment plan is a vast improvement over known systems that take up to eight months to pay a service provider.

This method contemplates that the medical service can be service related to a health procedure. This can be an operation or an out-patient procedure. It can apply to prescription filing; medical examinations, medical tests, medical diagnosis, eye glass prescriptions, dental examinations, dental procedures, mental health procedures, mental health therapies, physical therapy, podiatrists, doctor's visits, hospital visits, out-patient visits, and combinations of these and other procedures that have not been named.

This method contemplates that the smart card can be used to determine if a second opinion is required by the insurer for a medical service.

Now and with reference to the figures, FIG. 1 shows a diagram of the overall invention.

In FIG. 1, a person obtains medical insurance from the insurer (100) and obtains a service provider contract (101). A smart card is created (110). The smart card is used to see if the person if eligible for funds (120). If the user is eligible, the process proceeds. If they are not approved, the process ends. The smart card is next used to see if the medical service is preauthorized (130). Again, if the medical service is not preauthorized, the method ends. The smart card is next used to see if service provider is preauthorized (140). If all of the eligibility and preauthorization is met, the process proceeds. The smart card is used to facilitate a first transmission from the service provider to the insurer. A second transmission is made from insurer to service provider, which can include information on the preauthorized services (160). A third transmission is made from service provider to insurer acknowledging various items including payments (170) from the insured. Finally, payment is transferred from the insurer to the service provider (180).

The smart card also contains information on whether the person is eligible for accelerated funding from the insurer for medical services based on the insurance coverage. It also contains information on whether the person is eligible for accelerated funding to their service provider based on preauthorization from the insurer. The card can link via the chip to the insurer's database to obtain information on whether a service provider is preauthorized by the insurer to perform a medical service.

Figure 2:
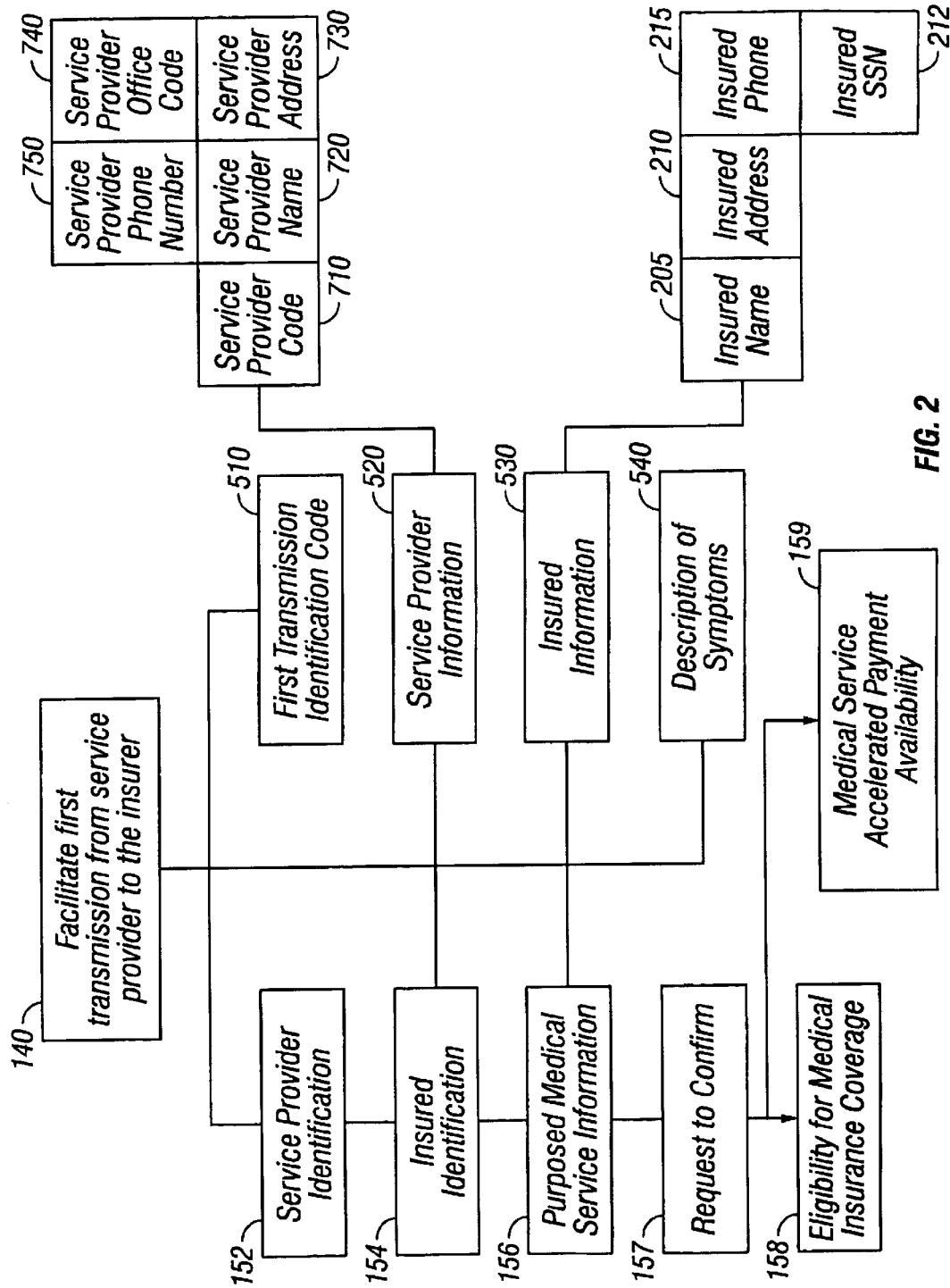
FIG. 2 is a diagram of the first transmission.

As shown in FIG. 2, the smart card facilitates the transmission of medical cost information via a first transmission to the insurer (140). The first transmission includes service provider identification (152), insured identification (154), proposed medical service information (156), and a request to confirm (157). The request to confirm (157) involves a request for eligibility for medical insurance coverage (158) and a request for medical service accelerated payment availability (159).

Further shown in FIG. 2, the first transmission (140) can also include a first transmission identification code (510), service provider information (520), insured information (530), and description of symptoms of insured (540). The service provider information (520) includes service provider code (710), service provider name (720), service provider address (730), service provider office code (740), and service provider phone number (750). The insured information includes insured name (205), insured address (210), insurer phone (215), and insured social security number (212). The first transmission can include all or a combination of these elements.

Figure 3:
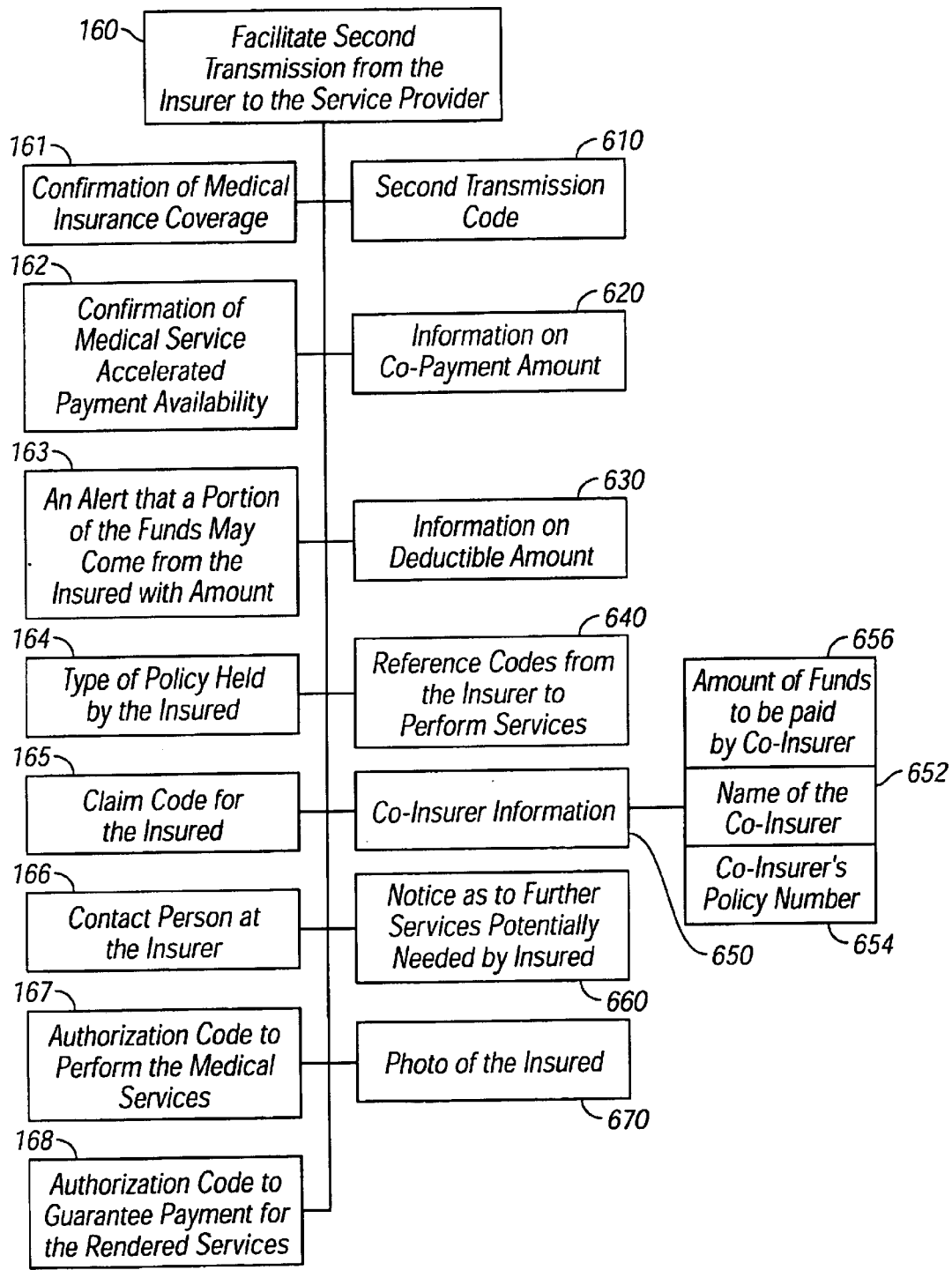
FIG. 3 is a diagram of the second transmission.

As shown in FIG. 3, the smart card can be used to facilitate a link to the insurer's database to obtain information in a second transmission (160) that concerns the amount of payment required by the person to the service provider based on the insurance coverage. The second transmission (160) includes confirmation of medical insurance coverage (161), confirmation of medical service accelerated payment availability (162), an alert to the service provider that a portion of the funds may need to come from the insured and an indication of that fund amount (163), type of policy held by the insured (164), claim code for the insured (165), contact person at the insurer (166), and authorization code to perform the medical services (167) and authorization to guarantee payment for the rendered services (160).

Further shown in FIG. 3, the second transmission (160) can also include a second transmission identification code (610), information on co-payment amount (620), information on deductible amount (630), reference codes from the insurer to be used by the service provider to perform the services (640), co-insurer information (650), a notice as to further services potentially needed by the insured (660), and a photo of the insured (670). The co-insurer information can further include the name of the co-insurer (652), co-insurer's policy number (654), and amount of funds to be paid by the co-insurer (656). The second transmission can include all or a combination of these elements.

Figure 4:
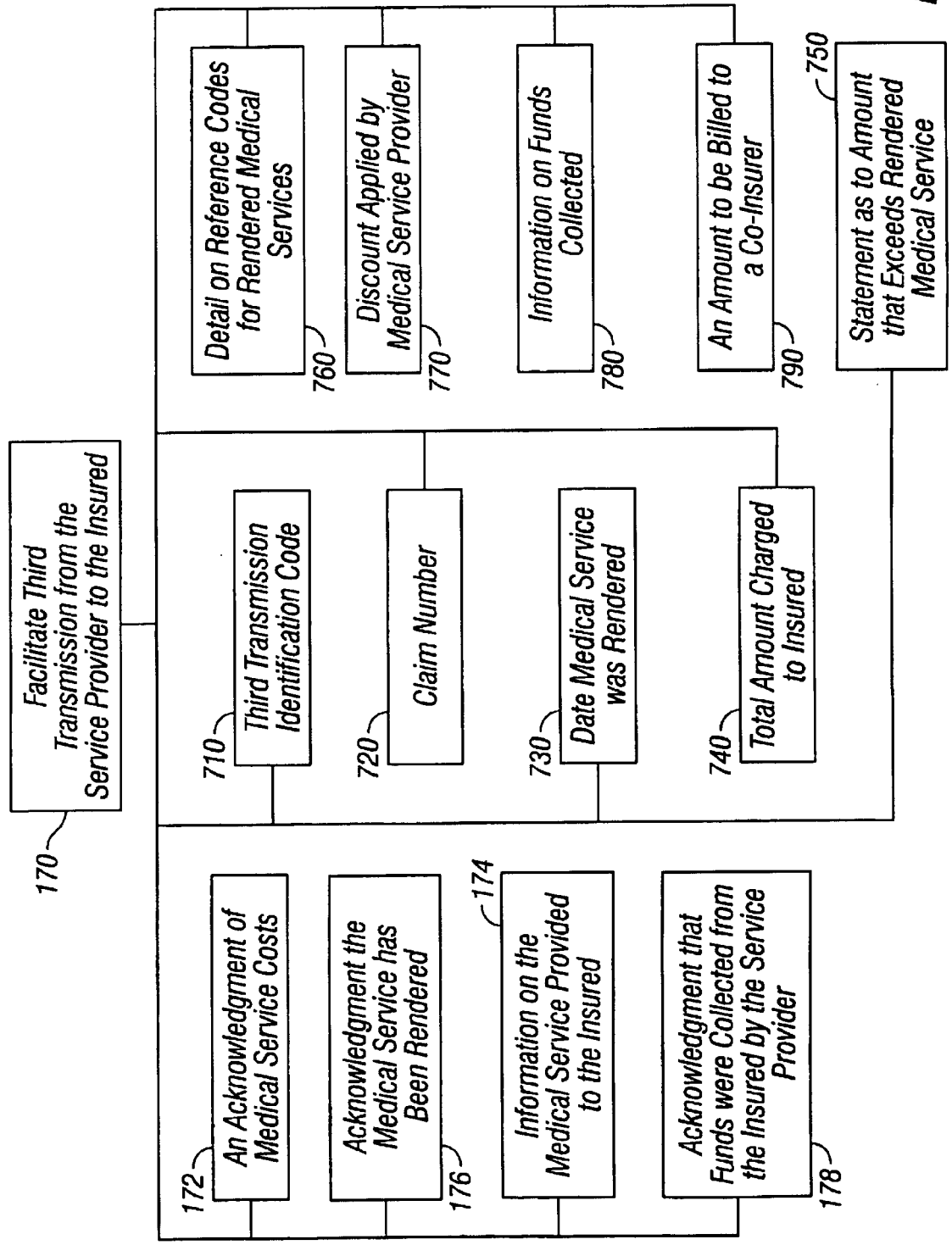
FIG. 4 is a diagram of the third transmission.

As shown in FIG. 4, the smart card can then be used to facilitate a third transmission (170) from the service provider to the insurer that contains an acknowledgement of the medical service costs (172), information on the medical service provided to the insured (174), acknowledgement that the medical service has been rendered from the service provider to the insured (176), and acknowledgement that funds were collected from the insured by the service provider (178).

Further shown in FIG. 4, the third transmission (170) can also include a third transmission identification code (710), claim number (720), date medical service was rendered (730), total amount charged to insured (740), statement as to amount that exceeded approved medical service costs (750), detail on reference codes for rendered medical services (760), discount applied by the medical services provider for a rendered medical service (770), information on funds collected which includes co-payment amount collected and deductible amount collected (780), and an amount to be billed to a co-insurer (790). The third transmission can include one or a combination of these elements.

Finally, and on approximately the same day that the third transmission is received by the insurer, funds are transmitted to the service provider's bank account from the insurer for the medical service provided to the person.

Other information that can be communicated to the insured includes transmitting the annual and ever-to-date insurers, co-payers, and deductible payment history and additional insurers report. The complete medical history, including diagnosis, treatments, and prognosis, can be communicated to the insured in a concise report.

The information shared in this process is readily available to the insured. The insured can ask the service provider for any of these corresponding reports during a visit. The hard ware (card reader) and/or software (reporting and accessing program) in the possession of the service provider give access to these reports at a time of their choosing.

Figure 5:
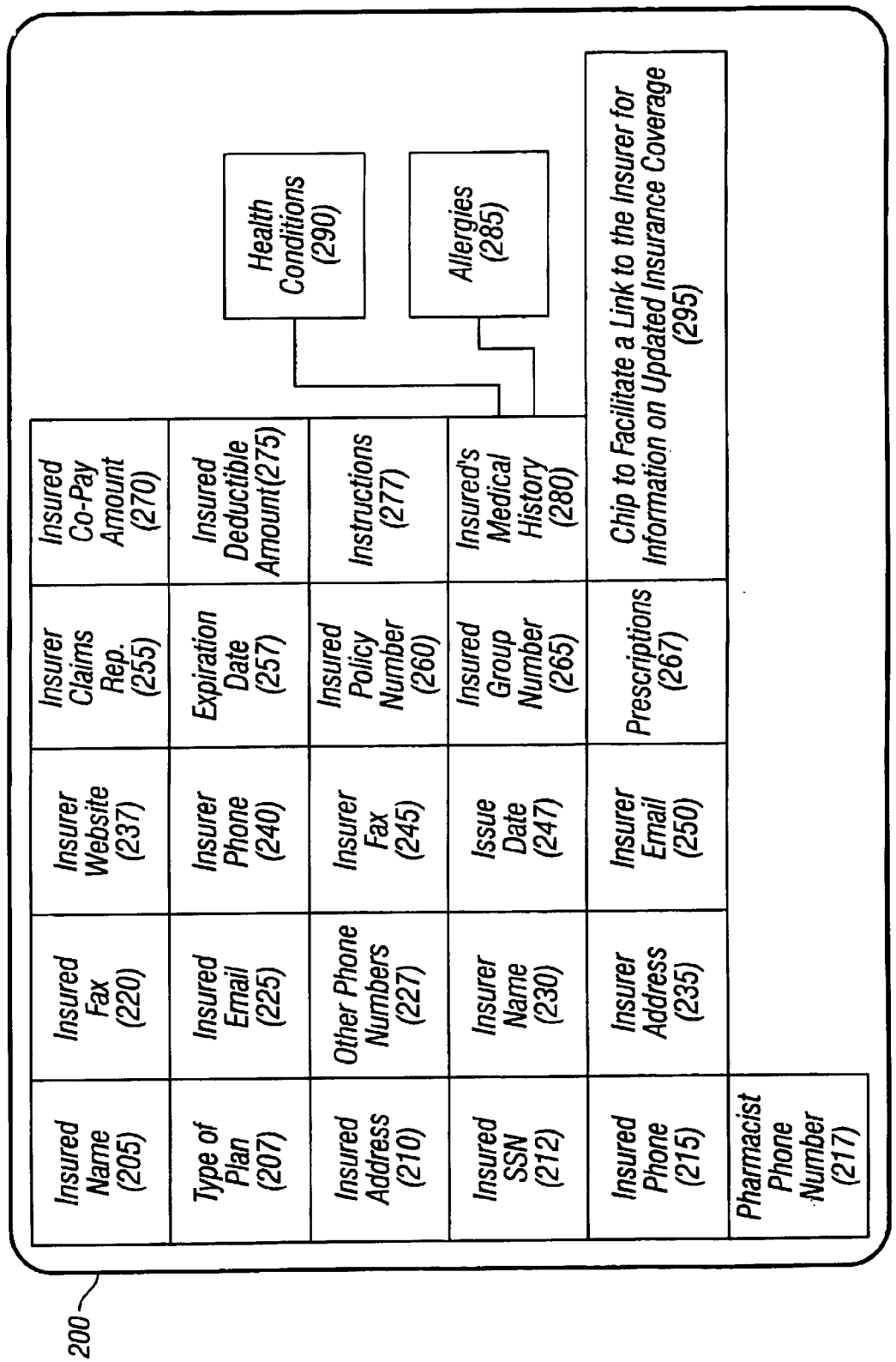
FIG. 5 is a diagram of a smart card usable in the invention.

FIG. 5 shows a smart card that is contemplated as within the scope of the invention.

In FIG. 5, the smart card (200) contains the insured name (205); type of plan (207); insured address (210); insured social security number (212); insured phone (215); pharmacist phone number (217); insured fax (220); insured email (225); other phone number (227); insurer name (230); insurer address (235); insurer website (237); insurer phone (240); insurer fax (245); issue date of card (247); insurer e-mail (250); insurer claims representative (255); expiration date of card (257); insured policy number (260); insured group number (265); prescriptions of insured (267); insured's co-pay amount (270); insured deductible amount (275); insured's medical history (280) that can include allergies (285) and health conditions (290); instructions on how to proceed (277); and a chip to facilitate a link to the insurer for information on updated insurance coverage (295).

Figure 6:
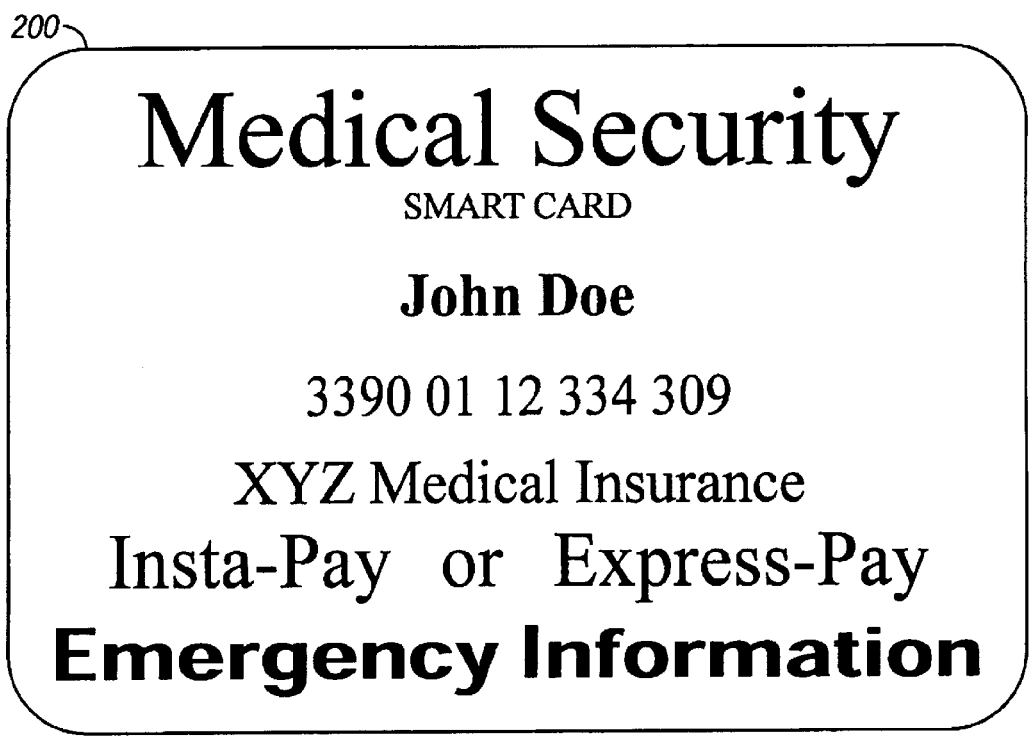
FIG. 6 is a picture of a smart card.

FIG. 6 shows an example of a smart card (200).

The smart card (200) includes numerous security devices to protect the user. Electronic fingerprinting and fingerprint recognition is a currently believed secure method of identification. This is far more secure than PIN codes that can be obtained even when encrypted relatively easily. Social security numbers are generally not considered secure. It is necessary for the individual who owns the smart card to have unique identifiers to allow access to the information on the card. Using first a fingerprint encoding device, the fingerprint or fingerprints of the owner of the card are loaded onto the non re-writable portion of the card's chip. A fingerprint reader connected to the card reader matches the real time image of the fingerprint (s) to the stored image and then provides electronic verification that the card and its owner are together at the same time. The owner can then enter a PIN code or other security code that will allow access to the information on the card by the then approved reader. The owner's authorization allows information to be shared between approved parties.

In the same way the fingerprint devices and stored images can be used for matching, other verification and authorization recognition devices can be used as well. Lazar or optical retinal scanning and facial recognition scanning uses the same techniques with different equipment. First, the image of the retina of the owner's eye is scanned and recorded permanently onto the chip of the card in a non-changeable location and format. At the time of verification a scanner is used to scan the card owner's retina in real time and compare the recorded image to the real time one. If there is a match then the owner's identity is verified and they can proceed to provide other authorizations as above.

Facial recognition works in the same manner as retinal scanning as does several other from of "optical" recognition and verification. The smart card (200) is contemplated to have all of these security measures.

While this invention has been described with emphasis on the preferred embodiments, it should be understood that within the scope of the appended claims the invention might be practiced other than as specifically described herein.

What is claimed is:

1. A method for accelerating the provision of funds to a service provider for medical insurance using a smart card, consisting of the steps of:
   a. obtaining medical insurance coverage from an insurer for a person;
   b. creating a relationship with at least one service provider for medical services for persons contracting with the insurer;
   c. creating a smart card for the person, wherein the smart card comprises: information about medical insurance coverage for the person and a personal identification code;
   d. using the smart card to determine if the person is eligible for accelerated provision of funds from the insurer to a service provider for medical services based on medical insurance coverage;

e. using the smart card to determine if a medical service is preauthorized by the insurer for the person;

d. using the smart card to determine if a service provider is preauthorized by the insurer to perform a medical service; and g. using the smart card to facilitate a first transmission from the service provider to the insurer, wherein the first transmission consists of:
  i. service provider identification;
  ii. insured information;
  iii. proposed medical service information,
  iv. a request to confirm for
    1. eligibility for medical insurance coverage;
    2. medical service accelerated payment availability;
  v. a first transmission identification code; and
  vi. a description of a symptom;

h. using the smart card to facilitate a second transmission from the insurer to the service provider, wherein the second transmission comprises:
  i. confirmation of medical insurance coverage;
  ii. confirmation of medical service accelerated payment availability;
  xii. an alert to the service provider that a portion of the funds may need to come from the insured and an indication of that fund amount;
  iv. type of policy held by the insured;
  v. claim code for the insured;
  vi. contact person at the insurer;
  vii. authorization code to perform the medical services and to guarantee payment for the rendered services;
  viii. information on co-payment amount;
  ix. information on deductible amount;
  x. reference codes from the insurer to be used by the service provider to perform the services;
  xi. co-insurer information;
  xii. a notice as to further services potentially needed by the insured;
  xiii. a depiction of the insured;
  xiv. a second transmission identification code, or combinations thereof;

i. using the smart card to facilitate a third transmission to the insurer from the service provider, wherein the third transmission comprises:
  i. an acknowledgement of the medical service costs,
  ii. information on the medical service provided to the insured,
  iii. acknowledgement that the medical service has been rendered from the service provider to the insured, and
  iv. acknowledgement that funds were collected from the insured by the service provider;
  v. claim number
  vi. date medical service was rendered;
  vii. total amount charged to insured;
  viii. statement as to amount that exceeds rendered medical service;
  ix. detail on reference codes far rendered medical services;
  x. discount applied by the medical a services provider for a rendered medical service;
  xi. information on funds collected which includes co-payment amount collected and deductible amount collected;
  xii. an amount to be billed to a co-insurer;
  xiii. a third transmission identification code; or
  xiv. combinations thereof; and j. from zero to two days from the third transmission being received by the insurer, funds are transmitted from the insurer to the service provider for the medical service provided to the person.

2. The method of claim 1, wherein the
  a. service provider information is at least one of
    i. service provider code;
    ii. service provider name,
    iii. service provider address;
    iv. service provider office code; and
    v. service provider phone number;
  b. insured information is a member of the group:
    i. insured name;
    ii. insured address;
    iii. insurer phone; and
    iv. insured social security number.

3. The method of claim 1, wherein the co-insurer information is at least one of:
  a. name of the co-insurer;
  b. co-insurer's policy number; and
  c. amount of funds already paid by the co-insurer.

4. The method of claim 1, wherein the funds are a member of the group: all of a co-payment fee, part of the co-payment fee, a deductible fee and combinations thereof.

5. The method of claim 1, wherein the medical insurance coverage is selected from the group: government medical insurance coverage and private medical insurance coverage.

6. The method of claim 1, wherein the insurer is an entity that has been authorized by the federal government or a state board of insurance to deliver insurance benefits for medical care.

7. The method of claim 1 wherein the person is a member of the group comprising: the primary insured, a spouse, at least one dependent, and combinations thereof.

8. The method of claim 7, wherein the primary insured is an animal.

9. The method of claim 8, wherein the animal is a registered pure bred animal.

10. The method of claim 1, wherein the smart card is an electronically readable card comprising information selected from the group:
  a. insured name;
  b. insured address;
  c. insured phone;
  d. insured fax;
  e. insured email;
  f. insured social security number;
  g. insurer name;
  h. insurer address;
  i. insurer phone;
  j. insurer fax;
  k. insurer e-mail;
  l. insurer claims representative;
  m. insured policy number;
  n. insured group number;
  o. insured type of plan;
  p. insured co-pay amount;
  q. insured deductible amount;
  r. insured's medical history;
  s. pharmacist phone number;

t. prescriptions of insured;

u. other phone numbers;

v. instructions on how to contact insurer;

w. expiration date;

x. insurer website;

y. a chip to link to the insurer for information on updated insurance coverage; and z. combinations thereof.

11. The method of claim 10, wherein the insured's medical history includes information on health allergies, and health problems.

12. The method of claim 10, wherein a completed authorized medical service is a service which has been authorized by contract by the insurer or is a stated item of coverage in an insurance policy.

13. The method of claim 1, wherein the funds are for a completed authorized medical service.

14. The method of claim 1, wherein the information about insurance coverage comprises a member of the group: dental coverage, medical coverage, date premiums were paid, date premiums are due, a code to link to the insurer's database to access medical payment schedules, and the insurer's database advance payment policies and combinations thereof.

15. The method of claim 1, wherein the medical service is selected from the group: a health related procedures, prescription filing; medical examinations, medical tests, medical diagnosis, eye glass prescriptions, dental examinations, dental procedures, mental health procedures, mental health therapies, physical therapy, podiatrists, doctor's visits, hospital visits, out-patient visits, and combinations thereof.

16. The method of claim 1, wherein the smart card can be used to determine if a second opinion is required by the insurer for a medical service.

\* \* \* \* \*